United States Patent
Howard et al.

(10) Patent No.: US 11,324,421 B2
(45) Date of Patent: May 10, 2022

(54) IMPAIRMENT DETECTION WITH ENVIRONMENTAL CONSIDERATIONS

(71) Applicant: 3M INNOVATIVE PROPERTIES COMPANY, St. Paul, MN (US)

(72) Inventors: James W. Howard, Circle Pines, MN (US); Eric C. Lobner, Woodbury, MN (US); Jennifer F. Schumacher, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 522 days.

(21) Appl. No.: 15/511,318

(22) PCT Filed: Sep. 15, 2015

(86) PCT No.: PCT/US2015/050072
§ 371 (c)(1),
(2) Date: Mar. 15, 2017

(87) PCT Pub. No.: WO2016/044198
PCT Pub. Date: Mar. 24, 2016

(65) Prior Publication Data
US 2017/0245782 A1 Aug. 31, 2017

Related U.S. Application Data

(60) Provisional application No. 62/050,367, filed on Sep. 15, 2014.

(51) Int. Cl.
*A61B 5/11* (2006.01)
*A61B 5/00* (2006.01)
*G16H 20/30* (2018.01)

(52) U.S. Cl.
CPC .............. *A61B 5/11* (2013.01); *A61B 5/0004* (2013.01); *A61B 5/4088* (2013.01);
(Continued)

(58) Field of Classification Search
CPC ....... A61B 5/11; A61B 5/1123; A61B 5/4023; A61B 5/4076; A61B 5/4082;
(Continued)

(56) References Cited

U.S. PATENT DOCUMENTS

| 5,137,345 A | 8/1992 | Waldorf |
| 5,295,491 A | 3/1994 | Gevins |

(Continued)

FOREIGN PATENT DOCUMENTS

| EP | 1642248 | 4/2006 |
| EP | 2319410 | 5/2011 |

(Continued)

OTHER PUBLICATIONS

US 7,877,241 B2, 01/2011, Elmer (withdrawn)
(Continued)

*Primary Examiner* — Devin B Henson
(74) *Attorney, Agent, or Firm* — Steven A. Bern; Christopher D. Karlen (57) ABSTRACT

A method and system for monitoring impairment indicators. The method comprises, during a first time window, measuring a first movement signal related to movement of a person with a movement sensor associated with the person, and measuring a first environmental signal with an environmental sensor. The method further comprises electronically storing at least one numerical descriptor derived from the first movement signal and the first environmental signal as reference data for the person. The method further includes, during a second time window, measuring a second movement signal related to movement of the person with the movement sensor and measuring a second environmental signal with the environmental sensor; and comparing at least one numerical descriptor derived from the second movement (Continued)

signal and the second environmental signal to the reference data to identify an impairment indicator.

21 Claims, 3 Drawing Sheets

(52) U.S. Cl.
CPC .......... *A61B 5/6803* (2013.01); *A61B 5/6804* (2013.01); *A61B 5/6805* (2013.01); *A61B 5/6828* (2013.01); *A61B 5/7275* (2013.01); *A61B 5/746* (2013.01); *G16H 20/30* (2018.01); *A61B 5/0002* (2013.01); *A61B 5/1123* (2013.01); *A61B 5/4023* (2013.01); *A61B 5/6829* (2013.01); *A61B 2503/20* (2013.01); *A61B 2560/0223* (2013.01); *A61B 2560/0242* (2013.01); *A61B 2560/0247* (2013.01); *A61B 2560/0252* (2013.01); *A61B 2562/0219* (2013.01)

(58) Field of Classification Search
CPC ... A61B 5/4088; A61B 5/4845; A61B 5/6803; A61B 5/6804; A61B 5/6805; A61B 5/6828; A61B 5/6829; A61B 5/7275; A61B 5/746; A61B 2503/20; A61B 2503/22; A61B 2560/0242; A61B 2560/0223; A61B 2562/0219; G06F 19/3481; G08B 21/02; G08B 21/0438; G08B 21/0423; A63B 24/0006; A63B 2024/0009; A63B 2024/0012; A63B 2024/0015; A42B 3/046
See application file for complete search history.

(56) References Cited

U.S. PATENT DOCUMENTS

| | | | |
|---|---|---|---|
| 5,325,862 A | 7/1994 | Lewis | |
| 5,354,120 A | 10/1994 | Volkle | |
| 5,421,344 A | 6/1995 | Popp | |
| 5,447,166 A | 9/1995 | Gevins | |
| 5,485,402 A | 1/1996 | Smith | |
| 5,724,987 A | 3/1998 | Gevins | |
| 6,032,530 A | 3/2000 | Hock | |
| 6,511,443 B2 | 1/2003 | Cuce | |
| 6,853,304 B2 | 2/2005 | Reisman | |
| 7,421,369 B2 | 9/2008 | Clarkson | |
| 7,451,056 B2 | 11/2008 | Flentov | |
| 7,512,515 B2 | 3/2009 | Vock | |
| 7,653,508 B1 | 1/2010 | Kahn | |
| 7,750,815 B2 | 7/2010 | Burris | |
| 7,818,131 B2 | 10/2010 | Mott | |
| 7,881,902 B1 | 2/2011 | Kahn | |
| 8,036,851 B2 | 10/2011 | Vock | |
| 8,078,334 B2 | 12/2011 | Goodrich | |
| 8,187,209 B1 | 5/2012 | Giuffrida | |
| 8,226,574 B2 | 7/2012 | Whillock | |
| 8,830,068 B2* | 9/2014 | Campbell | A61B 5/1118 340/573.1 |
| 10,321,870 B2* | 6/2019 | Nevo | A61B 5/165 |
| 2002/0052541 A1 | 5/2002 | Cuce | |
| 2003/0208335 A1 | 11/2003 | Unuma | |
| 2005/0001728 A1* | 1/2005 | Appelt | G08B 21/182 340/573.1 |
| 2005/0027216 A1 | 2/2005 | Guillemaud | |
| 2006/0235642 A1 | 10/2006 | Vock | |
| 2006/0284979 A1 | 12/2006 | Clarkson | |
| 2007/0010720 A1 | 1/2007 | Mott | |
| 2007/0063850 A1* | 3/2007 | Devaul | A61B 5/0024 340/573.1 |
| 2007/0112287 A1 | 5/2007 | Fancourt | |
| 2007/0124135 A1 | 5/2007 | Schultz | |
| 2007/0173727 A1 | 7/2007 | Naghavi | |
| 2007/0208530 A1 | 9/2007 | Vock | |
| 2007/0225614 A1 | 9/2007 | Naghavi | |
| 2007/0265816 A1 | 11/2007 | Elmer | |
| 2008/0183388 A1 | 7/2008 | Goodrich | |
| 2009/0069722 A1 | 3/2009 | Flaction | |
| 2009/0150114 A1 | 6/2009 | Vock | |
| 2009/0212957 A1 | 8/2009 | Burris | |
| 2009/0240462 A1 | 9/2009 | Lee | |
| 2009/0240463 A1 | 9/2009 | Lee | |
| 2009/0293615 A1 | 12/2009 | Lee | |
| 2009/0316983 A1 | 12/2009 | Han | |
| 2010/0016754 A1 | 1/2010 | Whillock | |
| 2010/0161706 A1 | 6/2010 | Kim | |
| 2010/0191155 A1 | 7/2010 | Kim | |
| 2010/0241464 A1* | 9/2010 | Amigo | A61B 5/1038 705/4 |
| 2011/0029250 A1 | 2/2011 | Mott | |
| 2011/0029465 A1 | 2/2011 | Ito | |
| 2011/0077919 A1 | 3/2011 | Lee | |
| 2011/0213276 A1 | 9/2011 | Sarussi | |
| 2012/0004883 A1 | 1/2012 | Vock | |
| 2012/0259578 A1 | 10/2012 | Bevilacqua | |
| 2012/0316406 A1 | 12/2012 | Rahman | |
| 2014/0088378 A1 | 3/2014 | Muzet | |
| 2015/0100135 A1* | 4/2015 | Ives | A61B 5/112 623/25 |
| 2016/0007910 A1* | 1/2016 | Boss | A61B 5/6803 600/301 |

FOREIGN PATENT DOCUMENTS

| | | |
|---|---|---|
| GB | 2447647 | 9/2008 |
| IN | 2389/CHE/2009 | 4/2011 |
| JP | 04250141 | 9/1992 |
| JP | 2009023545 | 2/2009 |
| KR | 20100073802 | 7/2010 |
| KR | 20100087551 | 8/2010 |
| KR | 20110034828 | 4/2011 |
| RU | 2146494 | 3/2000 |
| WO | WO 1993-07809 | 4/1993 |
| WO | WO 1995-18565 | 7/1995 |
| WO | WO 2005-118516 | 12/2005 |
| WO | WO 2007-107491 | 9/2007 |
| WO | WO 2008-091621 | 7/2008 |
| WO | WO 2009-090584 | 7/2009 |
| WO | WO 2009-117687 | 9/2009 |
| WO | WO 2009-117703 | 9/2009 |
| WO | WO 2009-151711 | 12/2009 |
| WO | WO 2013-136251 | 9/2013 |
| WO | WO 2014-083490 | 6/2014 |

OTHER PUBLICATIONS

Dai, "Mobile Phone Based Drunk Driving Detection", Pervasive Computing Technologies for Healthcare, 2010, pp. 1-8.
Grolsch, "Walk the Line IPhone App", [retrieved from the internet on May 15, 2017], URL <http://www.youtube.com/watch?v=YMagZK__Yoo>, pp. 1-2.
Intelligent Fingerprinting, "Rapid, non-invasive drug screening at the touch of a fingertip", [retrieved from the internet on May 15, 2017], URL <http://www.intelligentfingerprinting.com/>, p. 1.
National Highway Traffic Safety Administration, "Assessing the Feasibility of Vehicle-Based Sensors to Detect Alcohol Impairment", U.S. Department of Transportation, 2010, pp. 1-98.
National Institutes of Health, "Remote Monitoring System for Detecting Cocaine Ingestion/Intoxication (R01)", Department of Health and Human Services, 2011, pp. 1-14.
Rassnick, "Responding to acoustic startle during chronic ethanol intoxication and withdrawal", Psychopharmacology, 1992, vol. 106, No. 03, pp. 351-358.
Simmersion, "Training People For Important Conversations", [retrieved from the internet on May 15, 2017], URL <http://www.alcoholmonitoring.com/index/clients/overview>. pp. 1-4.
Verstraete, "Detection Times of Drugs of Abuse in Blood, Urine, and Oral Fluid", Basel Proceedings, 2004, vol. 26, No. 02, pp. 200-205.

(56) References Cited

OTHER PUBLICATIONS

International Search Report for PCT International Application No. PCT/US2015/050072, dated Dec. 18, 2015, 7 pages.

* cited by examiner

IMPAIRMENT DETECTION WITH ENVIRONMENTAL CONSIDERATIONS

TECHNICAL FIELD

The present invention relates to the field of recognizing or classifying movement, and more specifically, to identifying impairment indicators using both data from a movement sensor and data from an environmental sensor.

BACKGROUND

Detection of cognitive, physical, mental, sensory, emotional, or developmental impairment is critically important in healthcare, law enforcement, or other applications. Detection techniques may be specific to an individual impairment (such as physical) or any combination of impairments (such as cognitive and sensory). For example, detecting alcohol or controlled substance use or abuse by workers, individuals on parole, or in other contexts is important for safety and compliance with various restrictions. Detecting physical impairment, such as an injury, is important for workers who require full physical capabilities to perform their duties. Mental impairment detection is important in potentially diagnosing patients with the early onset of mind debilitating conditions such as dementia and/or Alzheimer's disease. Detecting other impairments such as tiredness, distraction, and vestibular confusion play an important role for safety and compliance purposes. Improved method for effectively monitoring for the presence of impairment without being invasive would be welcome.

SUMMARY

The present disclosure provides a new method of detecting impairment indicators using data from both a movement sensor and an environmental sensor. The present invention provides for non-intrusive continuous detection of impairment indicators using multiple inputs. Upon detection of an impairment indicator, a person may be required to perform further testing activities, thus reducing the overall need for and cost of types of impairment testing such as drug or alcohol screening. Impairment detection is also useful to proactively identify and mitigate potential safety situations. Identification and notification when an individual is impaired may reduce the amount of injuries or accidents that could occur otherwise. Additionally, using impairment detection for identifying diseases may lead to more effective treatment. Use of an environmental sensor in combination with a movement sensor improves impairment detection by calibrating the device based on movement parameters with ranges of environmental conditions, which eliminates false positives in impairment detection.

In one aspect, the present invention includes a method for monitoring impairment indicators. The method comprises, during a first time window, measuring a first movement signal related to movement of a person with a movement sensor associated with the person, and measuring a first environmental signal with an environmental sensor. The method further comprises electronically storing at least one numerical descriptor derived from the first movement signal and the first environmental signal as reference data for the person. The method further includes, during a second time window, measuring a second movement signal related to movement of the person with the movement sensor and measuring a second environmental signal with the environmental sensor; and comparing at least one numerical descriptor derived from the second movement signal and the second environmental signal to the reference data to identify an impairment indicator.

In some embodiments, the first time window occurs during a training activity performed by the person.

In some embodiments, the method further comprises collecting location information and using the location information as an additional factor to identify an impairment indicator.

In some embodiments, the impairment indicator is indicative of at least one of mental impairment, visual impairment and physical impairment.

In some embodiments, the environmental sensor includes at least one of a thermometer, a hygrometer, a sound meter, a particulate matter sampler, and an air quality meter.

In some embodiments, the environmental signal measures at least one of temperature, air quality, humidity, sound level and particulate level.

In some embodiments, impairment includes at least one of physical injury, vestibular confusion, distraction and prohibited substance abuse.

In some embodiments, the movement sensor is at least one of: an accelerometer, a gyroscope, a piezoelectric vibration sensor, a geographical positioning sensor and a magnetic switch.

In some embodiments, the movement sensor is attached to the person.

In some embodiments, when an impairment indicator is detected, at least one of a local alarm and a remote alarm is triggered.

In another aspect, the current disclosure includes a device for monitoring impairment indicators. The device comprises a housing configured to be attached to or carried by a person; an environmental sensor; and a processing unit disposed in the housing comprising a processor and a movement sensor. During a first time window, the movement sensor measures a first movement signal related to movement of the person and the environmental sensor measures a first environmental signal. The processor stores at least one numerical descriptor derived from the first movement signal and at least one numerical descriptor derived from the first environmental signal as reference data for the person. During a second time window, the movement sensor measures a second movement signal related to movement of the person and the environmental sensor measures a second environmental signal. The processor compares at least one numerical descriptor derived from the second movement signal and at least one numerical descriptor derived from the second environmental signal to the reference data to identify an impairment indicator.

In some embodiments, the housing is one of: a safety garment, a harness, a head-worn piece, a device to be attached to a limb of the person or a device used by the person.

In some embodiments, the device further includes a location module, and wherein the processor is configured to estimate a location of the person using at least both of a signal from the movement sensor and data from the location module.

In some embodiments, the device further uses the location of the person as a second factor to identify an impairment indicator.

In some embodiments, the impairment indicator is indicative of at least one of mental impairment, visual impairment and physical impairment.

In some embodiments, the movement sensor is at least one of: an accelerometer, a gyroscope, a piezoelectric vibration sensor, a geographical positioning sensor and a magnetic switch.

In some embodiments, the device comprises more than one movement sensor.

In some embodiments, the movement of the person during the first time window is walking.

In some embodiments, when an impairment indicator is detected, at least one of a local alarm and a remote alarm is triggered.

In some embodiments, the environmental sensor is at least one of: a thermometer, a hygrometer, a sound meter, a particulate matter sampler, and an air quality meter.

In some embodiments, the environmental signal is at least one of temperature, humidity, air quality, sound level and particulate levels.

BRIEF DESCRIPTION OF DRAWINGS

The following figures provide illustrations of the present invention. They are intended to further describe and clarify the invention, but not to limit scope of the invention.

Like numbers are generally used to refer to like components. The drawings are not to scale and are for illustrative purposes only.

DETAILED DESCRIPTION

Figure 1:
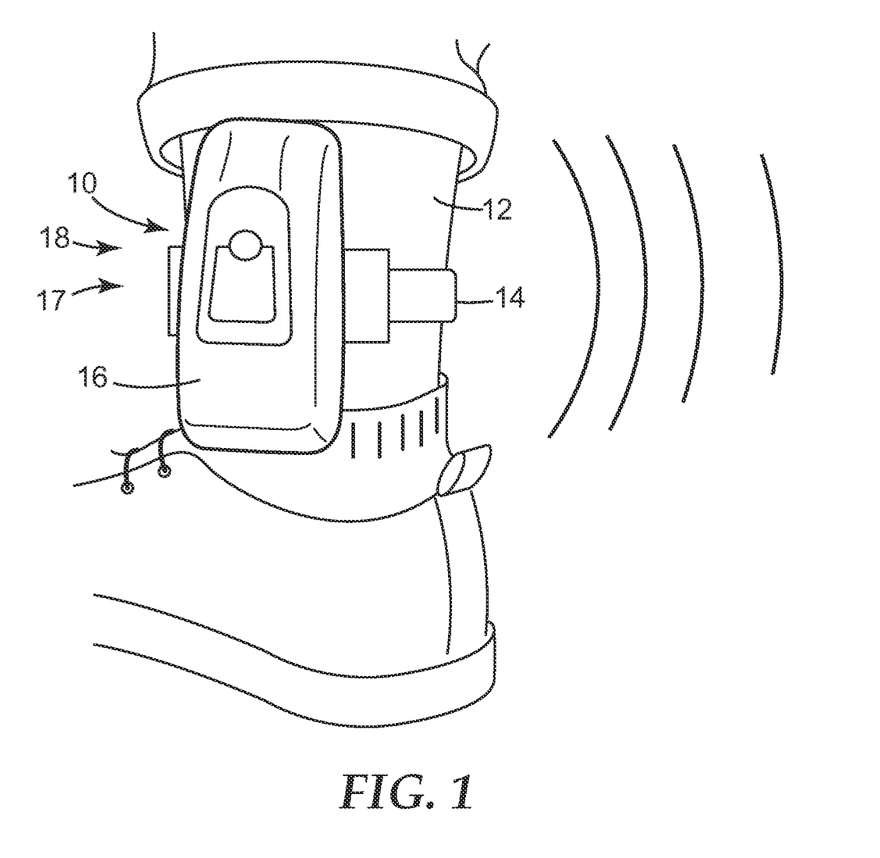
FIG. 1 is an example of a device for monitoring impairment indicators attached to a person.

FIG. 1 is an example of a device 10 for monitoring impairment indicators attached to a person's ankle 12. Device 10 is attached to person's ankle 12 or other limb with strap 14. The housing 16 for device 10 includes or contains a variety of components such as a processing unit 17, including a processor, a movement sensor, and an environmental sensor and a communication unit 18 for communicating wirelessly with an external device. In some embodiments, the environmental sensor may be in a separate device that is in communication with device 10. The processing unit may also include a location unit for determining a location of the user of device 10. A processor in the processing unit 17 may also include memory for storing data received from the movement sensor, numerical descriptors, reference data, and other necessary information to identify impairment indicators. The movement sensor may include at least one of a variety of sensors, including an accelerometer, gyroscope, piezoelectric vibration sensor, geographical positioning sensor and a magnetic switch. The environmental sensor may include at least one of a variety of sensors, including thermometer, a hygrometer, a sound meter, a particulate matter sampler, and an air quality meter.

A movement sensor may be configured to measure a signal related to movement of the person during a first time window. The movement sensor may collect data at a variety of rates, for example, the rate may be in the range of one (1) Hz to sixty (60) Hz. The rate may be, for example, 5 Hz, 10 Hz, 20 Hz, 30 Hz, 40 Hz, 50 Hz or 60 Hz or more. The length of the time window may be any desired range. For example, a time window may be in the range of two (2) seconds to ten (10) seconds. A time window may be, for example, 2 seconds, 5 seconds, 6 seconds, 10 seconds, or more or less. The number of samples taken by a movement sensor in the device varies based on the length of the time window and the sampling rate. The number of samples may range, for example, from 8 to 1024 samples. A processor may then electronically store at least one numerical descriptor derived from the first movement signal as reference data for the person. The numerical descriptor may be represented as a scalar such as a voltage, current, power, or energy measurement.

The environmental sensor can be configured to measure an environmental signal of the person during the first time window. The environmental signal may be, for example, temperature, air quality, humidity, sound level and particulate level. The environmental sensor may collect data at a variety of rates, as appropriate for each sensor. For example, a temperature sensor may not need to take a read more than once per every few minutes; however, a sound meter may need to read data many times per second. The frequency of sensor data collection is application specific. The environmental sensor may collect data at the same rate or at different rates from the movement sensor. The environmental sensor may collect the data during the same time window that the movement sensor is collecting data, or during a time window that differs in time or length from the movement sensor data collection. A processor may then electronically store at least one numerical descriptor derived from the first environmental signal along with the numerical descriptor derived from the first movement signal as reference data.

The movement sensor may then measure a second signal related to movement of the person during a second time window. The environmental sensor may then measure a second signal related to person. The processor may then compare at least one numerical descriptor derived from the second movement signal and at least one numerical descriptor derived from the second environmental signal to the reference data to identify an impairment indicator.

In one configuration, the first time window occurs during a training activity performed by the person. In some embodiments training activity may include, but is not limited to, a person completing a series of prescribed or predetermined movements to establish baseline performance data. In another configuration, the first time window is during normal use of the device 10 by the person.

Device 10 may also include other components such as a location unit that enables the device to receive satellite signals and determine location using, for example, GPS or the Global Navigation Satellite System (GLONASS) as discussed in U.S. Pat. No. 6,853,304 to Reisman et al., incorporated herein by reference. A location unit may use other location technologies such as triangulation using local WiFi signals or other known location technologies to estimate location of the activity recognition device 10, and thereby the location of the person wearing the device.

While device 10 is shown as having a housing of a device to be attached to a limb of the person, the housing may be a variety of embodiments. For example, the housing may also be a safety garment, safety equipment, a harness, a head-worn piece, and article of clothing or incorporated into a handheld or portable device to be used by the person such as a mobile phone.

While the housing for device 10 shows the movement sensor, environmental sensor, processor and other device components being located in close proximity to each other, in other housing configurations, the environmental sensor, the movement sensor, or multiple environmental or movement sensors, may be located in multiple locations in the housing, and located at a distance from other components, including being located at a distance from the processor and communication unit. In this configuration, the movement sensor and the environmental sensor are still able to communicate with the other components through a wired or wireless communication connection. In some configurations, the environmental sensor may be located remotely from device 10 and may be in communication with device 10. In some configurations, a particular environment, such as a work site, may have multiple environmental sensors, and device 10 may be in communication with more than one sensor, and may choose to communicate with the sensor in closest proximity to device 10.

Figure 2A:
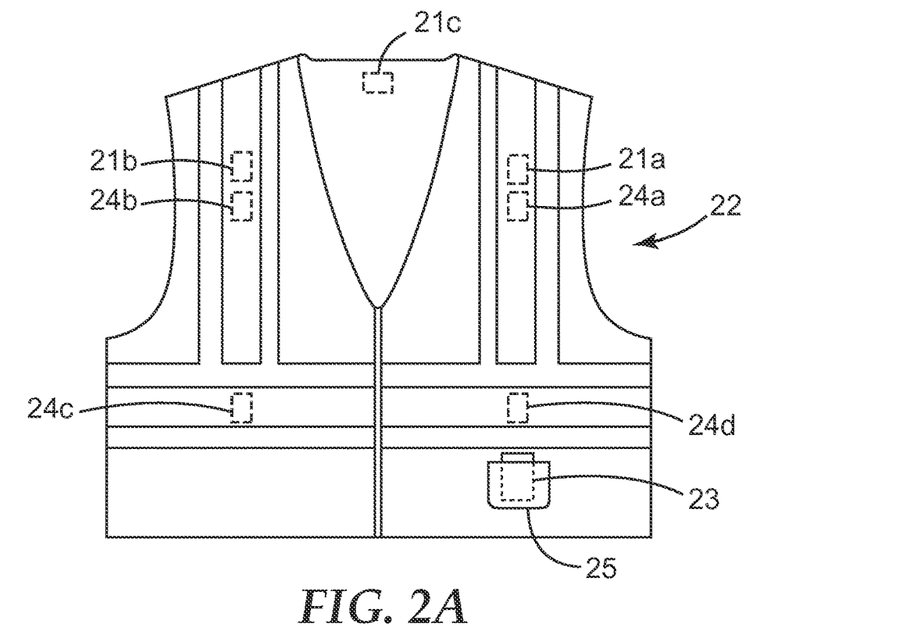
FIGS. 2a and 2b are examples of housings for a device for monitoring impairment indicators.
Figure 2B:
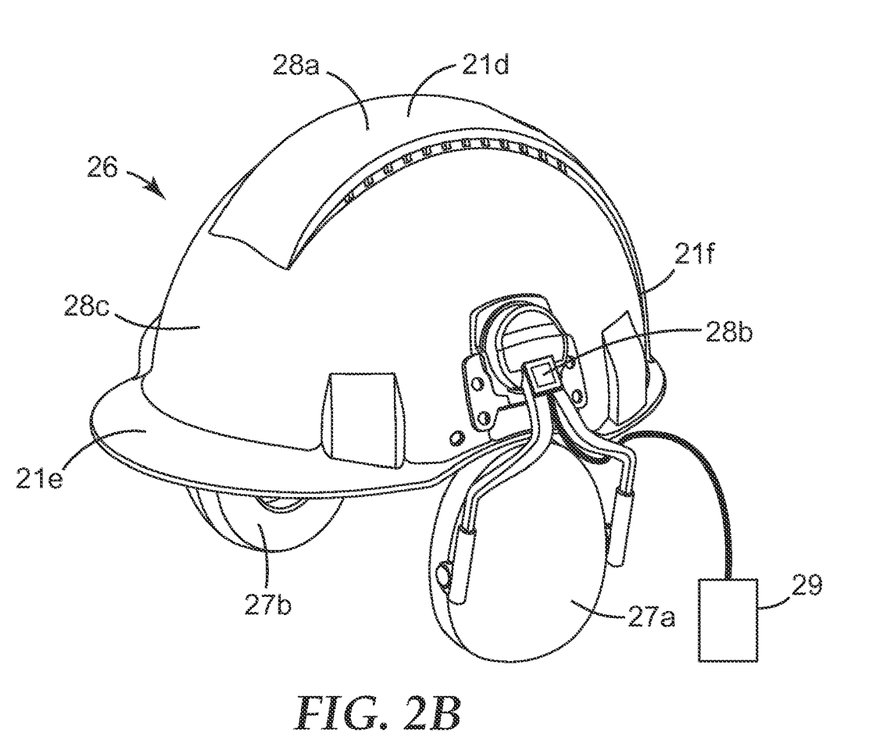

FIGS. 2a and 2b are examples of housings for a device for monitoring impairment indicators. FIG. 2a shows a high visibility safety vest 22. Vest 22 is a typical component of personal protective equipment (PPE) for many occupations and tasks, including construction, mining, road work, and in other fields and contexts. Vest 22 ensures that the wearer can be easily seen by, for example, other workers, oncoming vehicles and drivers of equipment. Vest 22 may also be a housing for a device for detecting impairment indicators. Movement sensors may be embedded at various locations in the vest, for example, at locations 24a, 24b, 24c, and 24d. The variety of locations allows for increased reliability of movement data. Environmental sensors 21a, 21b and 21c can also be embedded within the vest 22, or otherwise worn by the user. In some configurations, environmental sensors may be located in a place where they detect conditions of ambient air or other features of an environment that a user is working or present in without receiving interference from a user associated with the environmental sensor. Vest 22 may be designed to include a pocket or other holding mechanism to carry other components of an impairment monitoring device. Pocket 23 provides an exemplary accessible enclosure for components such as the processor, communication unit, battery and other components that may be enclosed in a single unit 25. Unit 25 may communicate with movement sensors at locations 22a-22d and environmental sensors at 21a-21c through a wired connection embedded or enclosed in vest 22, or through a wireless connection.

FIG. 2b shows a hard hat 26 that also includes ear protection. Hard hat 26 is an important piece of PPE that may be worn for many occupations and tasks, including construction, mining, road work, along with other fields and contexts. Hard hat 26 includes hearing protection muffs 27a and 27b. In some instances, muffs 27a and 27b may include noise cancellation capabilities and/or a speaker or other communication-related components. Hard hat 26 may be a housing for an impairment monitoring device. For example, movement sensors may be located at various locations 28a, 28b, and 28c throughout hardhat 26 to allow for increased movement data reliability. Environmental sensors may be located at various locations throughout hardhat 26 such as at locations 21d, 21e and 21f.

Hard hat 26 may have a unit 29 including components such as a processor, communication unit, battery, and other components that may be enclosed in a single unit 29. Unit 29 may be in communication with movement sensors through a wired or wireless connection. In some instances, unit 29 is integrated into the structure of hard hat 26 and in other instances (as illustrated in FIG. 2b) it may be in a physically separate structure from hard hat 26, and connected to the movement sensors embedded in hard hat 26 by a wired or wireless connection.

Figure 3:
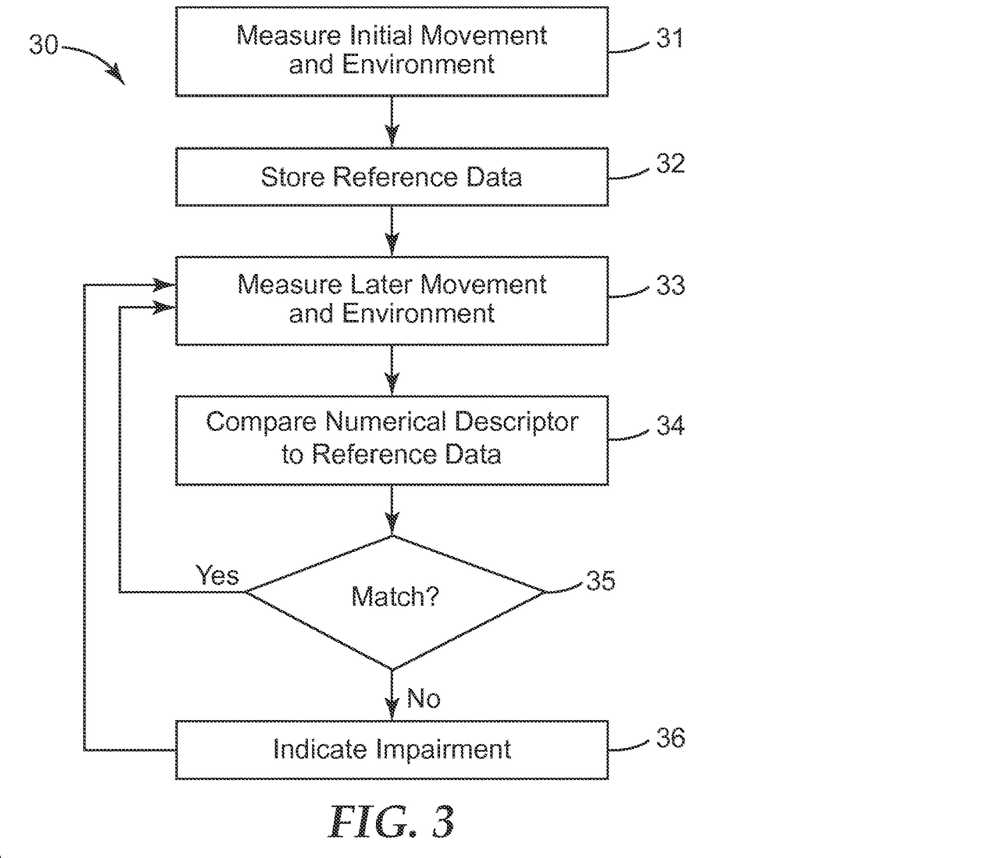
FIG. 3 is a flow chart representing a method of monitoring impairment indicators.

FIG. 3 is a flow chart representing a method of monitoring impairment indicators. The method includes, in step 31 measuring, with a movement sensor attached to a person, a first signal related to movement of the person during a first time window and measuring an environmental signal with a environmental sensor associated with the person during the first time window. The first movement signal and the first environmental signal may include a variety of information. For example, the signals may be the output of a capacitive accelerometer measured as a scalar voltage. The signals may also be the output of a piezoelectric accelerometer measured as a scalar current or voltage. The time window may be any given period of time over which to measure the first signal. As described above, the time window may be in the range of two seconds to ten seconds, and may be between those numbers, shorter or longer. In some instances, the movement sensor may measure the first signal over multiple time windows to increase the sample size which increases the accuracy of the measurement. In other instances, multiple sensors may each measure a signal related to movement of the person or multiple sensors may each measure a signal related to an environmental signal over the same time window. The plurality of data sets may increase reliability of measurement.

In some instances, the first time window occurs during a training activity performed by the person. A training activity may be completed through a series of prescribed motions while the device is placed into a special training mode. The training could be performed by an authorized trainer (e.g., a parole officer or a safety manager), and the trainer could show the person wearing the device a video instructing them on the types of movements to perform during the training period. After the training period is complete, the trainer returns the device to a normal monitoring mode.

In other instances, the movement of the person during the first time window occurs during their initial use of the impairment indicator device. In this case, the device begins detecting the movements of the person to capture the signals associated with the user defined movement. The device also detects an environmental signal during that time period to learn what typical movements in typical environments look like. The device then may detect anomalies when newly measured signals are compared to previously detected signals in similar environments. In some instances, the movement of the person during the first time window is walking, and in other instances, the movement may be another designated movement.

In step 32, the processor stores at least one numerical descriptor derived from each of the first movement signal and the first environmental signal as reference data for the person. In some configurations, the processor may combine the first movement signal and the first environmental signal to create a single numerical descriptor for the combined signal. The numerical descriptor is a number computed based on the data sampled from a signal measured by the movement sensor or by the environmental sensor. The numerical descriptor for each of the movement signal and the environmental signal may be based on a single measured signal or on multiple measured signals. For example, when the movement sensor detects inertial movement along three axes, the numerical descriptor may be calculated based on the data associated with one axis, any combination of two axes, a computation involving each of the three axes, or any combination thereof. The numerical descriptor may be determined for each data point related to the measured signal(s) or may be based on a lower sampling rate than the data from the measured signals. In some instances, two or more numerical descriptors may be associated with each time window.

The numerical descriptor may be stored as reference data, forming a baseline for the particular type of movement for the individual. For example, when the activity performed by the person during the first time window is walking, the numerical descriptor for their activity during at least the first time window is compared to future collected data to identify indication of impairment of the person at that future time.

In step 33, the movement sensor measures a second signal related to movement of the person during a second time window and the environmental sensor measures a second signal related to an environmental signal. The second time window may be chronologically adjacent to the first time window, or may be later in time. In some instances, the movement sensor and the environmental sensor may measure the second signal over multiple time windows to increase the sample size to provide a broader sample set for comparison to reference data. In other instances, multiple sensors may each measure a signal related to movement of the person over the same time window. The plurality of data sets may increase reliability of measurement.

In step 34, the processor compares at least one numerical descriptor derived from the second movement signal and at least one numerical descriptor derived from the second environmental signal to the reference data as a factor to identify an impairment indicator. In another embodiment, the movement signal and the environmental signal may be combined such that a single numerical descriptor is derived from the combined signal and then compared with the reference data. If there is alignment (within a tolerance) between the numerical descriptor and the reference data, the processor identifies normal behavior. Alignment may be determined by a simple thresholding process and may also be determined by using a multi-dimensional classification algorithm, in which case multiple numerical descriptors would be required. In step 35, the processor determines if a match exists between the two signals within a tolerance. If there are sufficient differences between the reference data and second signal and a match does not occur as defined in the "no" path of step 35, then the processor identifies an impairment indicator as shown in step 36. The parameters of detection of an impairment indicator can be tuned based on the application. Further, a tolerance may be tighter where accurate identification of impairment is critical or where there is a higher cost of impairment is mis-identified. An impairment indicator is indicative of at least one of mental impairment, visual impairment and physical impairment. These types of impairments may include specific impairments. For example, mental impairment includes at least distraction. Visual impairment includes at least prohibited substance abuse. And physical impairment includes at least physical injury and vestibular confusion.

If a match exists between the two signals as identified in the "yes" path of step 35 or no impairment indicator is identified as defined in step 36, the device continues to measure movement by returning to step 33. If an impairment indicator is detected, the device stores that result and in some instances, at least one of a local alarm and a remote alarm is triggered. The device then continues to measure movement as shown in step 33.

Figure 4:
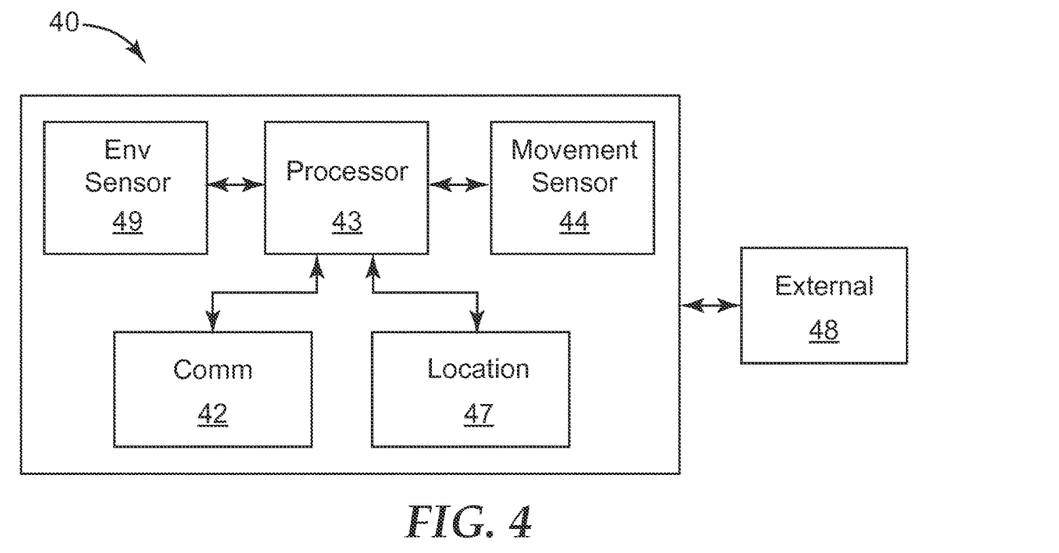
FIG. 4 is a block diagram of a device for monitoring impairment indicators.

FIG. 4 is a block diagram of a device 40 for monitoring impairment indicators. The device includes a processor 43, a movement sensor 44 and an environmental sensor 49. Processor 43 may be any type of processor or microprocessor commonly used to process information or to control a variety of other electronic components. Processor 43 interacts with movement sensor 44 to receive data from movement sensor 44, such as a signal related to the movement of the person wearing impairment monitoring device 40. Movement sensor 44 may be configured to measure such a signal during a time window as defined by processor 43. Processor 43 interacts with environmental sensor 49 to receive data from environmental sensor 49. Such as a signal related to an environmental signal of the person wearing impairment monitoring device 40. Environmental sensor 49 may be configured to measure such a signal during a time window as defined by processor 43.

Movement sensor 44 may be at least one of: an accelerometer, a gyroscope, a piezoelectric vibration sensor, a geographical positioning sensor and a magnetic switch. Movement sensor 44 may include more than one movement sensor. Movement sensor 44 measures a first signal related to movement of the person wearing impairment monitoring device 40 during a first time window. The processor 43 stores at least one numerical descriptor derived from the first signal as reference data for the person. In some embodiments, the processor 43 may store the reference data with an assigned activity label, such as walking, running, or biking.

Environmental sensor 49 may be at least one of: electrocardiography, electroencephalography, electromyography, galvanic skin response, pulse oximeter, pressure transducer, photo resister, and thermistor sensors. Environmental sensor 49 may include more than one environmental sensor. Environmental sensor 49 measures a first signal related to an environmental signal of the person wearing impairment monitoring device 40 during a first time window. The processor 43 stores at least one numerical descriptor derived from the first environmental signal as reference data for the person.

An exemplary time window may be in the range of 2 (two) seconds to 10 (ten) seconds and may contain a number of samples in the range of 8 (eight) to 1024 samples, as an example, not as a limitation. Each of environmental sensor 49 and movement sensor 44 may also be configured to operate in a very low power mode where sampling takes place occasionally over a longer time period, for example, once every five minutes, when the individual is sleeping or doing some other sedentary and longer-term activity. In general, data collection by the movement sensor 44 or environmental sensor 49 could range between 0.2 Hz and 50 Hz in frequency, but is not limited to previously defined range. The data collection frequency may be dependent upon the type of activity being detected. For example, faster moving activities, such as running, may require a higher sample rate (closer to 50 Hz) than slower moving activities such as sleeping. The size of a time window may also be related to data collection rate. A time window should have enough samples for the data collected to store as reliable reference data.

Movement sensor 44 then measures a second signal related to movement of the person during a second time window and processor 43 compares at least one numerical descriptor derived from the second movement signal to the reference data to identify an impairment indicator. Comparison may include an algebraic sum or difference or other statistical variation such as mean, standard deviation, or variance. In an embodiment, the first signal (or reference data) may be a voltage represented numerically as 3.3 volts and the second signal may be recorded (also numerically) as a voltage of 1.3 volts. Processor 43 may compute the absolute difference between the first and second signal as 2.0 volts and determine whether the variation is above or below a threshold that indicates impairment and triggers an alarm.

Environmental sensor 49 then measures a second signal related to movement of the person during a second time window and processor 43 compares at least one numerical descriptor derived from the second environmental signal to the reference data to identify an impairment indicator.

Movement sensor 44 and environmental sensor 49 may either be contained in the same physical unit as processor 43 or may be connected to processor 43 in a wired or wireless configuration.

Device 40 may further include a location unit 47. The location unit 47 may be any device that provides an estimated geographical location for impairment monitoring device 40. Examples of a location unit 47 include the following technologies: GPS, Cellular Triangulation, WiFi triangulation and GNSS. In some configurations, processor 43 may be configured to estimate a location of the person using at least both of the signal from the movement sensor and data from the location unit. In some configurations, device 40 may use the location of the person as estimated by location unit 47 as a second factor to identify an impairment indicator.

Device 40 may also include a communications unit 46 to allow device 40 to communicate with external devices 48. For example, when an impairment indicator is detected, a local alarm or a remote alarm in external device 48 may be triggered.

While not shown in FIG. 4, impairment monitoring device 40 may further include an emergency notification component. Emergency notification component may be triggered manually, such as by a button or switch. When emergency notification component is triggered, communication unit 46 may transmit information to external device 48. External device 48 may be a central monitoring system, an emergency alert system, or other location. The information transmitted may include the location of device 40, the time the emergency notification is transmitted, and the reason that the emergency notification is transmitted.

The signal from the movement sensor 44 is a digital representation (for example, a number between 0 and 1023) of an analog voltage output from the sensor describing the motion The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Variations on the disclosure described above will be apparent to one of skill in the art upon reading the present disclosure, and are intended to be included within the scope of the present disclosure. A wide range of activities may be detected in addition to those discussed explicitly herein, and are within the scope of the present disclosure. Further, a variety of analysis methods may be used consistent with the disclosed analysis steps and processes.

What is claimed is:

1. A method comprising:
   during a first time window, measuring a first movement signal related to movement of a worker with a movement sensor associated with the worker, and measuring a first environmental signal with an environmental sensor of a work site located remotely from the movement sensor;
   electronically storing at least one numerical descriptor derived from the first movement signal and the first environmental signal as reference data for the worker with a processor of a processing unit, the reference data forming a baseline for a particular type of movement of the worker;
   during a second time window, measuring a second movement signal related to movement of the worker with the movement sensor and measuring a second environmental signal with the environmental sensor, wherein the processing unit includes the movement sensor, and the processing unit is housed in a housing comprising a component of personal protection equipment (PPE) worn by the worker for an occupation;
   comparing at least one numerical descriptor derived from the second movement signal and the second environmental signal to the reference data to identify an impairment indicator indicating non-compliance with a safety restriction with the processor; and
   wherein the first time window occurs during a training activity performed by the worker.

2. The method of claim 1, further comprising collecting location information and using the location information as an additional factor to identify an impairment indicator.

3. The method of claim 1, wherein the impairment indicator is indicative of at least one of mental impairment, visual impairment and physical impairment.

4. The method of claim 1, wherein the environmental sensor includes at least one of a thermometer, a hygrometer, a sound meter, a particulate matter sampler, and an air quality meter.

5. The method of claim 1, wherein the environmental signal measures at least one of temperature, air quality, humidity, sound level and particulate level.

6. The method of claim 1, wherein the impairment indicator is indicative of prohibited substance abuse.

7. The method of claim 1, wherein the movement sensor is at least one of: an accelerometer, a gyroscope, a piezoelectric vibration sensor, a geographical positioning sensor and a magnetic switch.

8. The method of claim 1, wherein the movement sensor is attached to the worker.

9. The method of claim 1, wherein, when an impairment indicator is detected, at least one of a local alarm and a remote alarm is triggered.

10. The method of claim 1, wherein the training activity comprises the worker completing a series of predetermined movements to establish baseline performance data.

11. A device comprising:
a housing comprising personal protection equipment (PPE) configured to be attached to or carried by a worker;
an environmental sensor of a work site;
a processing unit disposed in the housing comprising a processor and a movement sensor, the environmental sensor located remotely from the movement sensor;
wherein, during a first time window, the movement sensor measures a first movement signal related to movement of the worker and the environmental sensor measures a first environmental signal;
wherein the processor stores at least one numerical descriptor derived from the first movement signal and at least one numerical descriptor derived from the first environmental signal as reference data for the worker, the reference data forming a baseline for a particular type of movement of the worker;
wherein, during a second time window, the movement sensor measures a second movement signal related to movement of the worker and the environmental sensor measures a second environmental signal;
wherein the processor compares at least one numerical descriptor derived from the second movement signal and at least one numerical descriptor derived from the second environmental signal to the reference data to identify an impairment indicator indicating non-compliance with a safety restriction; and
wherein the first time window occurs during a training activity performed by the worker.

12. The device of claim 11, wherein the housing is one of: a safety garment, a harness, or a hard hat.

13. The device of claim 11, wherein the device further includes a location module, and wherein the processor is configured to estimate a location of the worker using at least both of a signal from the movement sensor and data from the location module.

14. The device of claim 13, further comprising using the location of the worker as a second factor to identify an impairment indicator.

15. The device of claim 11, wherein the impairment indicator is indicative of at least one of mental impairment, visual impairment and physical impairment.

16. The device of claim 11, wherein the movement sensor is at least one of: an accelerometer, a gyroscope, a piezoelectric vibration sensor, a geographical positioning sensor and a magnetic switch.

17. The device of claim 11, wherein the device comprises more than one movement sensor.

18. The device of claim 11, wherein the movement of the worker during the first time window is walking.

19. The device of claim 11, wherein, when an impairment indicator is detected, at least one of a local alarm and a remote alarm is triggered.

20. The device of claim 11, wherein the environmental sensor is at least one of: a thermometer, a hygrometer, a sound meter, a particulate matter sampler, and an air quality meter.

21. The device of claim 11, wherein the environmental signal is at least one of temperature, humidity, air quality, sound level and particulate levels.

* * * * *